(12) United States Patent
Chen et al.

(10) Patent No.: US 8,343,771 B2
(45) Date of Patent: Jan. 1, 2013

(54) METHODS OF USING CYANINE DYES FOR THE DETECTION OF ANALYTES

(75) Inventors: Bingzhi Chen, Harleysville, PA (US); Caibin Xiao, Holliston, MA (US); Hong Xu, Shanghai (CN); Alan M. Agree, Morrisville, PA (US); Chunbo Yu, Shanghai (CN)

(73) Assignee: General Electric Company, Schenectady, NY (US)

( * ) Notice: Subject to any disclaimer, the term of this patent is extended or adjusted under 35 U.S.C. 154(b) by 67 days.

(21) Appl. No.: 13/005,134

(22) Filed: Jan. 12, 2011

(65) Prior Publication Data

US 2012/0178171 A1    Jul. 12, 2012

(51) Int. Cl.
G01N 21/77    (2006.01)
G01N 33/20    (2006.01)

(52) U.S. Cl. ............ 436/84; 436/73; 436/164; 436/166; 436/169; 422/420; 422/82.05; 422/82.09

(58) Field of Classification Search .................... 436/73, 436/84, 106, 109, 124, 125, 150, 164, 166, 436/169, 172; 422/420, 82.01, 82.05, 82.08, 422/82.09
See application file for complete search history.

(56) References Cited

U.S. PATENT DOCUMENTS

| | | |
|---|---|---|
| 3,709,662 A | 1/1973 | Hach |
| 3,770,735 A | 11/1973 | Stookey |
| 3,836,331 A | 9/1974 | Stookey |
| 4,092,115 A | 5/1978 | Rupe et al. |
| 4,129,479 A | 12/1978 | Morrow |
| 4,270,925 A | 6/1981 | Isa et al. |
| 4,308,027 A | 12/1981 | Ceriotti |
| 4,391,775 A | 7/1983 | Huber et al. |
| 4,514,504 A | 4/1985 | Rothman |
| 4,894,346 A | 1/1990 | Myers et al. |
| 4,938,926 A | 7/1990 | Reiss |
| 5,017,498 A | 5/1991 | Fossati et al. |
| 5,032,526 A | 7/1991 | Myers et al. |
| 5,120,661 A | 6/1992 | Baker et al. |
| 5,128,419 A | 7/1992 | Fong et al. |
| 5,155,048 A | 10/1992 | Williams et al. |
| 5,171,450 A | 12/1992 | Hoots |
| 5,236,845 A | 8/1993 | Pierce et al. |
| 5,242,602 A | 9/1993 | Richardson et al. |
| 5,300,442 A | 4/1994 | Frant |
| 5,342,787 A | 8/1994 | Bardsley et al. |
| 5,362,653 A | 11/1994 | Carr et al. |
| 5,389,548 A | 2/1995 | Hoots et al. |
| 5,491,094 A | 2/1996 | Ramana et al. |
| 5,593,850 A | 1/1997 | Wetegrove et al. |
| 5,645,799 A | 7/1997 | Shah et al. |
| 5,654,198 A | 8/1997 | Carrier et al. |
| 5,705,394 A | 1/1998 | Ananthasubramanian et al. |
| 5,736,405 A | 4/1998 | Alfano et al. |
| 5,763,287 A | 6/1998 | Itagaki et al. |
| 5,772,894 A | 6/1998 | Ward et al. |
| 5,783,149 A | 7/1998 | Serrat |
| 5,925,318 A | 7/1999 | Kruzel et al. |
| 5,958,788 A | 9/1999 | Johnson et al. |
| 5,972,713 A | 10/1999 | Kuzuhara et al. |
| 5,976,823 A | 11/1999 | Wu |
| 6,030,842 A | 2/2000 | Peachey-Stoner |
| 6,051,437 A | 4/2000 | Luo et al. |
| 6,180,412 B1 | 1/2001 | Kroll |
| 6,214,627 B1 | 4/2001 | Ciota et al. |
| 6,274,382 B1 | 8/2001 | Treiber |
| 6,331,438 B1 | 12/2001 | Aylott et al. |
| 6,355,489 B1 | 3/2002 | Carratelli |
| 6,524,350 B2 | 2/2003 | Buentello et al. |
| 6,627,450 B1 | 9/2003 | Taylor et al. |
| 6,689,618 B1 | 2/2004 | Chen |
| 6,777,242 B1 | 8/2004 | Gautier et al. |
| 7,087,150 B2 | 8/2006 | Feng |
| 7,723,120 B2 | 5/2010 | Xiao et al. |
| 2002/0192836 A1 | 12/2002 | Groger et al. |
| 2006/0029516 A1 | 2/2006 | Potyrailo |
| 2007/0092407 A1 | 4/2007 | Xiao et al. |
| 2007/0092972 A1 | 4/2007 | Xiao et al. |
| 2007/0092973 A1 | 4/2007 | Potyrailo et al. |
| 2008/0295581 A1 | 12/2008 | Zhang et al. |
| 2009/0044603 A1* | 2/2009 | Potyrailo et al. ............. 73/53.01 |

FOREIGN PATENT DOCUMENTS

| | | |
|---|---|---|
| EP | 0 135 298 A2 | 3/1985 |
| JP | 56104248 A | 8/1981 |
| WO | 9901737 | 1/1999 |
| WO | WO 01/38857 A1 | 5/2001 |
| WO | WO 2007/050463 A1 | 5/2007 |
| WO | WO 2008/150594 A1 | 12/2008 |
| WO | 2012016350 | * 2/2012 |

OTHER PUBLICATIONS

"Cyanine", Wikipedia, http://en.wikipedia.org/wiki/Cyanine, 4 pages, Sep. 20, 2010.

(Continued)

*Primary Examiner* — Maureen Wallenhorst
(74) *Attorney, Agent, or Firm* — Wegman Hessler & Vanderburg

(57) ABSTRACT

Measuring the concentration of an analyte in an aqueous solution by obtaining an aqueous solution containing an analyte, providing a cyanine indicator, placing the aqueous solution in fluid communication with the cyanine indicator, measuring a detectable property change of the cyanine indicator, and comparing the detectable property change of the cyanine indicator with a calibration curve of the detectable property change of samples containing known concentrations of the analyte. The concentration of the analyte is determined using the detectable property change that is proportional to the concentration of the analyte in the aqueous solution.

13 Claims, 10 Drawing Sheets

OTHER PUBLICATIONS

International Search Report and Written Opinion dated Jun. 1, 2012 in related application No. PCT/US2011/063371, filed Dec. 6, 2011.
Ehrengruger et al., "Arachidonic Acid and Other Unsaturated Fatty Acids Alter Membrane Potential in PC12 and Bovine Adrenal Chromaffin Cells" Journal of Neurochemistry, 60, 282-288 (1993).
Hanning et al., "Enhanced sensitivity of wavelength modulated surface plasmon resonance devices using dispersion from a dye solution" Sensors and Actuators, 54, 25-36 (1999).
Petty et al., "Thermodynamic Characterization of the Association of Cyanine Dyes with DNA" J. Phys. Chem., 104 7221-7227 (2000).

* cited by examiner

METHODS OF USING CYANINE DYES FOR THE DETECTION OF ANALYTES

RELATED APPLICATION

This application is related to U.S. application Ser. No. 11/809,345, now abandoned, filed May 31, 2007, and assigned to General Electric Company, which is herein incorporated by reference.

BACKGROUND OF THE INVENTION

1. Field of the Invention

This invention is related to the detection of analytes in industrial water systems with cyanine dyes.

2. Description of Related Art

Water is used in a number of industrial water systems such as cooling and boiler water systems. Municipal or untreated water contain substances which can affect heat transfer, fluid flow or cause corrosion of system equipment. The presence of these substances and any resulted scaling, biofouling and corrosion adversely affects the rate of heat transfer, and therefore the efficiency of the system. Accordingly, before the water is utilized for cooling or steam purposes, it is desirably treated with appropriate chemicals.

Chemical treatment of water is well developed and widely used. For example, it is known to add polyelectrolytes to the water to reduce scaling. One particularly useful polyelectrolyte is Coag139D (PMA, polymethacrylic acid); although other polyelectrolytes such as AEC (alcohol ether carboxylates), APES (alkylphenol ethoxylates) and HPS-I (hydroxypropyl sulfonate ether copolymers) are in use as well. However, the employment of polyelectrolytes in industrial water systems presents its own set of problems because the concentration of the polyelectrolytes in the water must be carefully monitored. For example, if too little of the polyelectrolytes is employed, scaling will occur. In contrast, if too high a concentration of the polyelectrolytes is employed, then the cost/performance efficiency of the system is adversely affected. As with other methods of chemically treating aqueous systems, there is an optimal concentration of treatment chemicals that should be maintained.

Several methods for determining the concentration of polyelectrolytes in aqueous systems are available. For example, there are several colorimetric methods for determination of polyelectrolytes using dyes. One example is U.S. Pat. No. 6,214,627 issued to Ciota et al, herein incorporated by reference. In addition, there is a Hach polyacrylic acid method that uses iron thiocyanate chelation to detect calibration based on polyacrylic acid. Generally, these methods require a complicated, multi-step operation procedure and are difficult to carry out in the field. Other methods, such as the one disclosed in U.S. Pat. No. 5,958,778 issued to Johnson et al., herein incorporated by reference, use luminol-tagged polymers in combination with fluorescent or chemiluminescent detection techniques to monitor the industrial waters. Also, there is a turbidity method that relies on the formation of insoluble compounds for determining the concentration of water-soluble polymers. This method is lengthy and is susceptible to inaccuracies.

Thus, there exists a strong need for simplified test methods that can easily be used to determine the concentration of analytes in industrial water sources.

SUMMARY OF THE INVENTION

The present invention concerns a method of measuring the concentration of an analyte in an aqueous solution that comprises the steps of: obtaining an aqueous solution containing an analyte, providing a cyanine indicator, placing the aqueous solution in fluid communication with the cyanine indicator, measuring a detectable property change of the cyanine indicator, and comparing the detectable property change of the cyanine indicator with a calibration curve of the detectable property change of samples containing known concentrations of the analyte to determine the concentration of the analyte, wherein the detectable property change is proportional to the concentration of the analyte in said aqueous solution.

The present invention and its advantages over the prior art will become apparent upon reading the following detailed description and the appended claims with reference to the accompanying drawings.

BRIEF DESCRIPTION OF THE DRAWINGS

These and other aspects of the invention will be understood from the description and claims herein, taken together with the drawings showing details of construction and illustrative embodiments, wherein:

DETAILED DESCRIPTION OF THE INVENTION

Figure 1A:
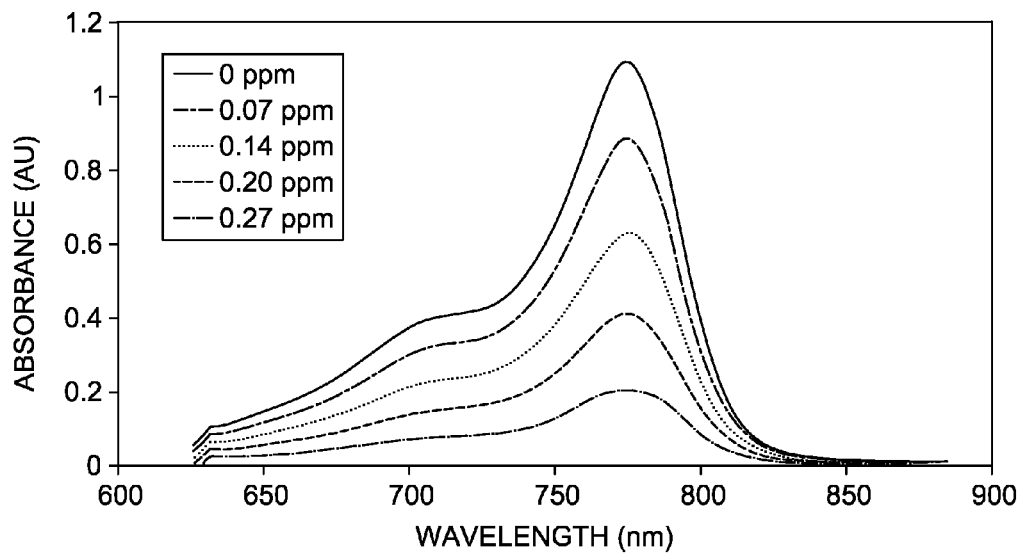
FIG. 1a depicts spectrums of aqueous solutions with different amounts of free chlorine at different pH values.

Approximating language, as used herein throughout the specification and claims, may be applied to modify any quantitative representation that could permissibly vary without resulting in a change in the basic function to which it is related. Accordingly, a value modified by a term or terms, such as "about", is not limited to the precise value specified. In at least some instances, the approximating language may correspond to the precision of an instrument for measuring the value. Range limitations may be combined and/or interchanged, and such ranges are identified and include all the sub-ranges stated herein unless context or language indicates otherwise. Other than in the operating examples or where otherwise indicated, all numbers or expressions referring to quantities of ingredients, reaction conditions and the like, used in the specification and the claims, are to be understood as modified in all instances by the term "about".

"Optional" or "optionally" means that the subsequently described event or circumstance may or may not occur, or that the subsequently identified material may or may not be present, and that the description includes instances where the event or circumstance occurs or where the material is present, and instances where the event or circumstance does not occur or the material is not present.

As used herein, the terms "comprises", "comprising", "includes", "including", "has", "having", or any other variation thereof, are intended to cover a non-exclusive inclusion. For example, a process, method, article or apparatus that comprises a list of elements is not necessarily limited to only those elements, but may include other elements not expressly listed or inherent to such process, method, article, or apparatus.

The singular forms "a", "an", and "the" include plural referents unless the context clearly dictates otherwise.

Disclosed are improved methods of using cyanine dye as an indicator for detecting the concentration of an analyte in an aqueous solution. The aqueous solution is a sample of water taken from an industrial water source including, but not limited to, cooling water, boiler water, wastewater, seawater, rainwater. The analyte capable of being detected using this method include, but are not limited to, one or more of free chlorine, total chlorine, iron (e.g., Ferric and/or ferrous), total iron, or polyelectrolytic (e.g., polyanionic, polycationic, such as COAg139D, or polymethacrylic acid, and polyDADMAC, or polydiallyldimethyldiammonium chloride). Preferably, the cyanine indicator used in this method has a long wavelength absorbance, such as IR-783 (2-[2-[2-chloro-3-[2-[1,3-dihydro-3,3-dimethyl-1-(4-sulfobutyl)-2H-indol-2-ylidene]-ethylidene]-1-cyclohexen-1-yl]-ethenyl]-3,3-dimethyl-1-(4-sulfobutyl)-3H-indolium hydroxide), IR-780 (1,1',3,3,3',3'-4,4',5,5'-di-benzo-2,2'-indotricarbocyanine perchlorate), IR-775 (2-[2-[2-chloro-3-[2-(1,3-dihydro-1,3,3-trimethyl-2H-indol-2-ylidene)-ethylidene]-1-cyclohexen-1-yl]-ethynyl]-1,3,3-trimethyl-3H-indolium chloride), and IR-746 (2-[7-[1,3-dihydro-3,3-dimethyl-1-(4-sulfobutyl)-2H-indol-2-ylidene]-hepta-1,3,5-trienyl]-3,3-dimethyl-1-(4-sulfobutyl)-3H-indolium hydroxide). It is anticipated that any cyanine indicator can be used that has a molar extinction coefficient higher than 100,000 (mol-1.cm-1) and sufficient stability and selectivity. A cyanine indicator is sufficiently stable when cyanine dyes are present in a solution and the absorbance at maximum peak is stable (less than about 1% change) over a time period of about 20 minutes. The selectivity required by a cyanine indicator will be made apparent from the examples below.

Applicants have discovered that cyanine indicator undergoes a detectable physical property change when exposed to an analyte in an aqueous solution. The physical property change is proportional to the concentration of the analyte in the aqueous solution. The main property change of the cyanine indicator when reacted with the analyte discussed herein is color, but any other detectable physical or chemical property change may be used, such as luminescence or electrochemistry. It is contemplated that the cyanine indicator can be aqueous, or can be contained in a film.

The concentration of an analyte in an aqueous solution can be measured by providing a cyanine indicator, placing an aqueous solution containing an analyte in fluid communication with the cyanine indicator, measuring a detectable property change of the cyanine indicator, and comparing the measured detectable property change with a calibration curve. The detectable property change is proportional to the concentration of the analyte in the aqueous solution. In embodiments that use color as the detectable property change, the absorbance of the cyanine indicator is compared with a calibration curve of the absorbance of samples containing known concentrations of the analyte to determine the concentration of the analyte.

In order to determine the concentration of an analyte in an aqueous solution, it is first necessary to generate a calibration curve for each analyte of interest. Further, if the response of the cyanine indicator is dependent upon the pH, it is also necessary to generate a calibration curve for each analyte of interest at the same pH level of the aqueous solution of interest. Calibration curves are generated by preparing various aqueous solutions containing known amounts of a analyte, placing the aqueous solutions in fluid communication with the cyanine indicator, and measuring the detectable property change. In one embodiment, the detectable property change is color, in which the absorbance is measured. For the purposes of this embodiment, absorbance is being reported as absorbance difference. Absorbance difference is the difference between the absorbance of the cyanine indicator by itself and the absorbance of the cyanine indicator after a sample of aqueous solution is placed in fluid communication with the cyanine indicator. The calibration curve is then a plot of this absorbance difference vs. the known concentration of the analyte for a known pH.

Once created, the calibration curve can be used to determine how much of an analyte is present in an aqueous solution by comparing the measured detectable response of the cyanine indicator with the calibration curve and reading the amount of analyte present off of the curve. In order to use the calibration curve, the device used to measure the detectable response must be the same or operate on similar conditions as the device that was used to create the calibration curve. If color is used as the detectable response, the absorbencies may be measured using any suitable device known in the art to measure absorbance. Such suitable devices include, but are not limited to, colorimeters, spectrophotometers, colorwheels, and other types of known color-comparator measuring tools. In one embodiment, absorbance measurements can be performed using a TrueSense device (from GE Betz of Trevose, Pa.), such as TrueSense PWA or TrueSense Online.

In one embodiment, in order to determine the concentration of analyte present in an aqueous solution using this method, between about 2000 μl and about 5 μl, desirably about 60 μl of the aqueous solution containing the analyte is placed in fluid communication with the cyanine indicator. Between about 70 μl and about 1 μl, preferably about 20 μl of the cyanine indicator is used. However, other amounts of aqueous solution and cyanine indicator are contemplated without departing from the scope of the invention.

The analyte in the aqueous solution is then allowed to react with the cyanine indicator for a period of time between about 30 seconds and about 10 minutes, preferably between about 1 minute and 8 minutes, most preferably at about 5 minutes. It has been found that the reaction is usually complete in about 5 minutes, making any detectable property change measurement taken at about 5 minutes and thereafter accurate. It has been found that this accurate detectable property change measurement taken at about 5 minutes remains essentially stable for about the first 20 minutes (less than about 1% change over time), with minor fluctuations occurring after about the first 20 minutes.

Once the detectable property change is measured (usually the absorbance difference described above), it is compared with calibration curves that show the standard detectable property change of aqueous solutions containing known amounts of the analyte. In this way, the amount of analyte present in the sample can be determined. In yet another embodiment, the detectable property change measurement is done continuously before exposure to the aqueous solution, during exposure to the aqueous solution, and after exposure to the aqueous solution.

The present disclosure will now be described more specifically with reference to the following examples. It is to be noted that the following examples are presented herein for purpose of illustration and description; they are not intended to be exhaustive or to limit the disclosure to the precise form disclosed.

EXAMPLE 1

Cyanine Dyes for F-Cl Detection Using Aqueous IR-783

There are number of scenarios in which free chlorine (F-Cl) and/or total chlorine have be monitored at very low concentration. For example, reverse osmosis (R.O.) is a technique for removing dissolved solids (salts) from filtered raw water. It is used in a variety of industries to condition water for plant use, or as a step in the demineralization process. The continued performance of a reverse osmosis system depends upon the condition of the semipermeable membrane. When free chlorine concentration is higher than about 0.02 ppm, it can degrade many membrane materials, so the raw water is often dechlorinated prior to entering the R.O. system.

Since raw water can contain either free or total chlorine, it is important to determine which form of chlorine is present, and select the right chlorine monitoring equipment. Accordingly, supersensitive detection methods are highly desired for the protection of reverse osmosis membranes.

Figure 1B:
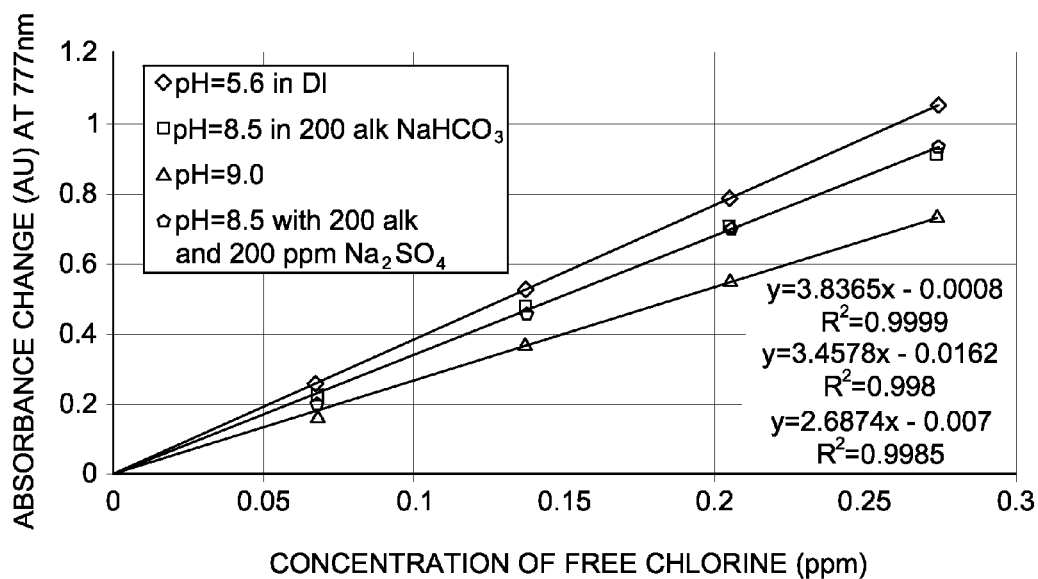
FIG. 1b depicts calibrations curve obtained for free chlorine using aqueous IR-783.

Turning to FIGS. 1a and 1b, disclosing one embodiment of this method, Applicants have found that several cyanine indicators having a pH range of 6-11, such as IR-783, IR-780, IR-775, IR-746, selectively react with free chlorine (F-Cl) if the counter anion is not Iodide. The F-Cl concentration is proportional to the decrease of absorbance of the cyanine indicator at long wavelengths, such as wavelengths of about 780 nm. These cyanine indicators allow for the detection of F-Cl at ultra-low ranges (about <0.1 ppm/100 ppb). The molar extinction coefficient of DPD, the standard colorimetric method for F-Cl detection, is around 9000 $L \cdot mol^{-1} \, cm^{-1}$. Accordingly, the theoretical DPD detection limit is around 0.02 ppm. On the other hand, IR dyes with high molar extinction coefficients (about 230,000 $L \cdot mol^{-1} \, cm^{-1}$) can theoretically detect as low as 0.001 ppm (1 ppb). FIG. 1a shows the spectra of an aqueous solution with differing amounts of F-Cl at different pH values. More specifically, the response of IR-783 to 0 to 270 ppb free-chlorine at pH 5.6, 8.5, and 9.0. FIG. 1b shows the calibration curve obtained for F-Cl by IR-783 at 777 nm at different pH values. FIG. 1b was obtained by subtracting the absorbance of a samples containing free chlorine at known concentrations from the absorbance of a sample containing no free chlorine. The response shown in FIG. 1a is used in conjunction with the calibration curve shown in FIG. 1b to ascertain the concentration of F-Cl in the aqueous solution samples.

Additionally, when a sample containing only chloramines is used, such as tap water, the absorbance at 780 nm is unaffected even with lengthened reaction time by chloramines. This demonstrates the selectivity of IR-783 to free-chlorine. Other cyanine dyes, such as IR-780, IR-755, and IR-746, which exhibit behavior similar to that of IR-783, can also be used. As expected, the response of the cyanine indicators to free chlorine is dependent upon the pH of the aqueous solution. Accordingly, calibration curves are used to account for this dependency.

EXAMPLE 2

Cyanine Dyes for F-Cl Detection using IR-783 in Solid pHEMA Film

Figure 2:
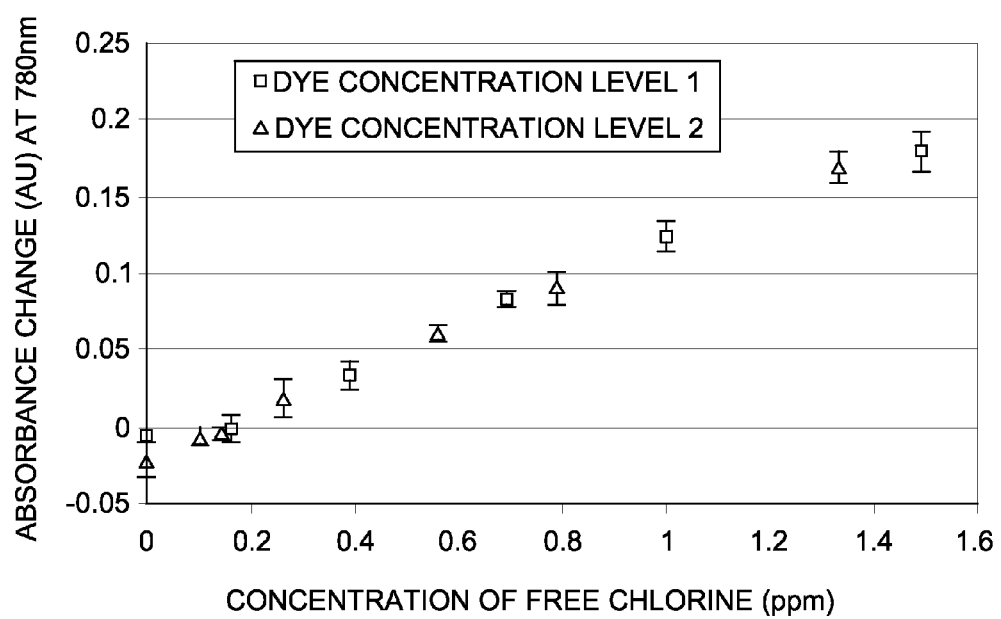
FIG. 2 depicts a calibration curve obtained for free chlorine using IR-783 in pHEMA film.

Applicants have also found that when IR-783 is incorporated into a film, the response to free-chlorine is identical to that of aqueous IR-783. In this example, the film was made from pHEMA stock in 2-methoxyethanol (or DM, or DM/PM mixture) containing IR-783 (5 mg to 20 mg per gram of pHEMA stock) by flow-coating. DM is di(ethylene glycol) monomethyl ether and PM is 1-Methoxy-2-Propanol. The dry film thickness could be from about 1 μm to about 20 μm. The film was assembled and exposed to standard F-Cl solutions and a TrueSense PWA reader was used to acquire the response. FIG. 2 shows the calibration curve obtained for IR-783 in pHEMA film at 780 nm. FIG. 2 was obtained by subtracting the absorbance of a samples containing free chlorine at known concentrations from the absorbance of a sample containing no free chlorine. In FIG. 2, dye concentration level 1 is 10 mg per 10 g of ink, and dye concentration level 2 is 20 mg per 10 g of ink. This demonstrates that IR-783 is sensitive enough to measure the F-Cl down to a level of 0.2 ppm. As can be seen, this level of sensitivity is exceptional for solid film sensors. Other cyanine dyes, such as IR-780, IR-755, and IR-746, which exhibit behavior similar to that of IR-783, can also be used.

EXAMPLE 3

Cyanine Dyes for T-Cl by IR-783 with KI

In this example, the total chlorine (T-Cl) is calculated using cyanine indicator dye, more specifically IR-783 in aqueous phase. T-Cl, the sum of both free and combined chlorine, can be determined by the DPD method after the addition of catalytic amounts of potassium iodide (KI) to the aqueous solution sample. In the DPD method, DPD (N,N-diethyl-p-phenylenediamine) is oxidized by chlorine, causing a magenta (red) color. The intensity of color is directly proportional to the chlorine concentration. For total chlorine, potassium iodide is added to the reaction to determine combined available chlorine forms and total chlorine. Chloramines oxidize the iodide to iodine; then the liberated iodine reacts with DPD to form the magenta color.

Monochloramine and dichloramine are very slowly reacts with cyanine dyes at near neutral pH. To quantify these species, the tests in this example were performed with iodide as catalyst. The iodide reacts with the chloramines to form iodine as the triiodide ion ($I_3^-$):

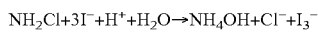

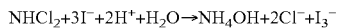

The triiodide, in turn, reacts with cyanine, forming the oxidized radical product with unique pink color or colorless decomposed species. In practice, only a trace of iodide is required to resolve monochloranmine. By adding excess iodide, dichloramine is included. Iodide could be directly from the cyanine itself if the counter ion is iodide. The iodide can also be introduced such as potassium iodide, tetramethylammonium iodide and etc.

Figure 3A:
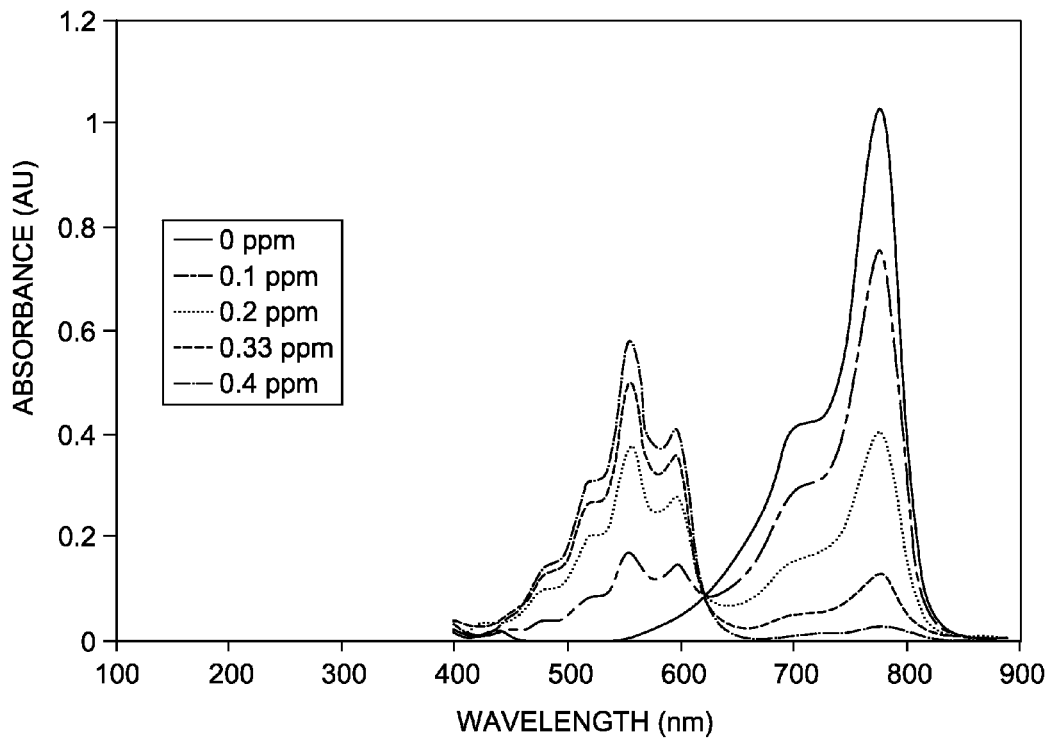
FIG. 3a depicts spectrums of aqueous solutions with different amounts of total chlorine.
Figure 3B:
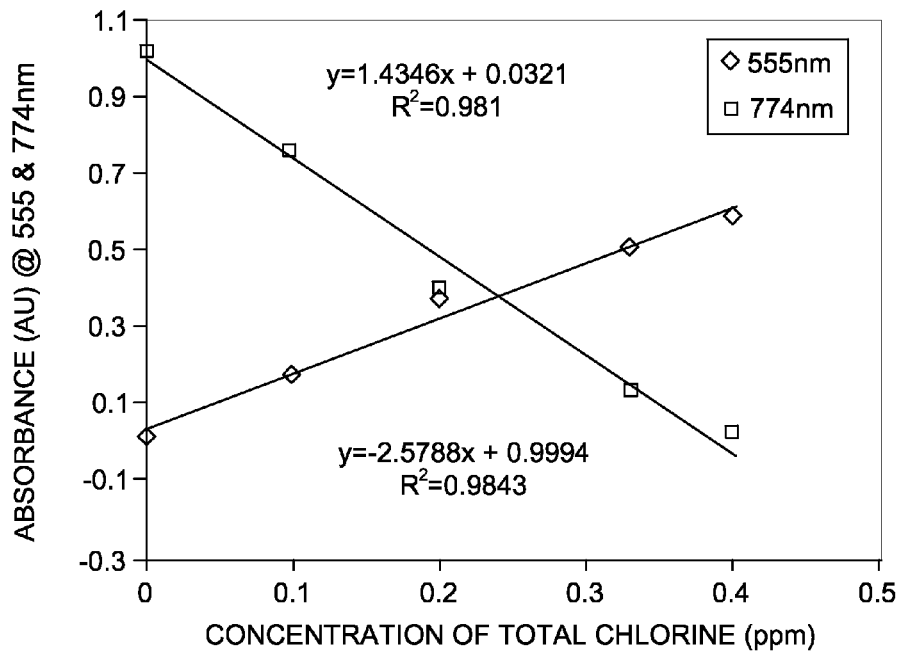
FIG. 3b depicts calibration curves obtained for total chlorine using IR-783.

It was observed that with the presence of KI, the IR-783 response to free and combined chlorine produced a purple color having a maximum peak around 555 nm with three shoulder peeks. Accordingly, the concentration of T-Cl is proportional to the generated purple color. FIG. 3a shows the spectra of an aqueous solution with differing amounts of T-Cl. More specifically, the response of IR-783 to T-Cl in the presence of KI. FIG. 3b shows the calibration curves obtained for T-Cl by IR-783 for 555 nm and 774 nm respectively. The response shown in FIG. 3a is used in conjunction with the calibration curve shown in FIG. 3b to ascertain the concentration of T-Cl in the aqueous solution samples.

This experiment was also performed using IR-780 and IR-775, which produced a similar result. It is also anticipated that other cyanine dyes, such as IR-746, which exhibit behavior similar to that of IR-780, IR-755, and IR-783, can also be used.

EXAMPLE 4

Cyanine Dyes for Iron (Ferric) Detection by IR-783

Both soluble and insoluble iron can be present in boiler feedwater and boiler water. Boiler water iron will deposit on the steam generating surfaces of the boiler and cause under-deposit corrosion and overheating problems. Thus the iron concentration in feedwater should be continuously monitored. Normally, the suggested Iron concentration in boiler feed water will range from 10 ppb to 100 ppb depending on the boiler pressure. This method can also be used for detecting iron, both Ferric and total iron, specifically at low concentration of iron (about <1 ppm).

At acidic conditions, Ferric ($Fe^{III}$) is a relative strong oxidant. For example, it can oxidize the iodide to iodine. Cyanine dyes are technologically important class of redox molecules that are commonly used as spectral sensitizers for photographic silver halide materials. Cyanine dyes can be oxidized by Ferric at acidic conditions either to it radical form or to decomposed compounds. If radical form was produced, a typical bathochromically shifted band will show around 550 nm with one or more shoulder peaks. Normally, the solution will turn from pale green color to dark pink with increasing Ferric concentration. Since the absorbance band intensity is proportional to the Ferric concentration, the absorbance at certain wavelengths can be used to back calculate Ferric concentration in unknown samples. The following equation depicts the reaction when cyanine dye was oxidized by Ferric to radical form. Compared to the original charge of the dye, the radical form of the cyanine dye is always one more positively charged.

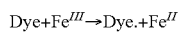

Figure 4A:
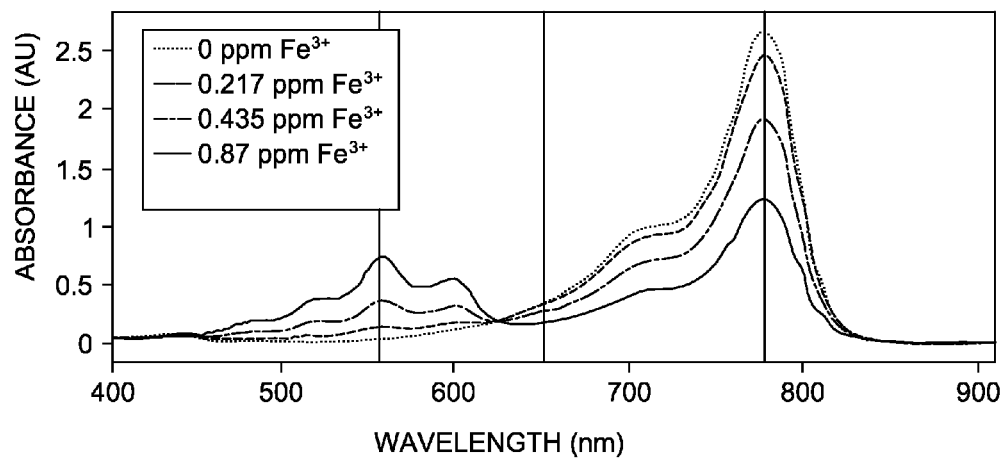
FIG. 4a depicts spectrums of aqueous solutions with different amounts of Ferric iron.
Figure 4B:
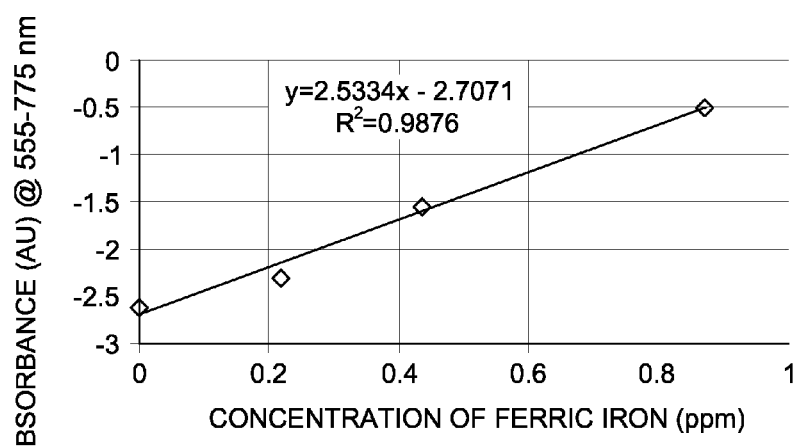
FIG. 4b depicts a calibration curve obtained for Ferric iron using IR-783.

In this example, FIG. 4a shows the spectra of an aqueous solution with differing amounts of Ferric. More specifically, the response of IR-783 at pH=3.6 to multiple aqueous solution samples having different concentrations of Ferric. FIG. 4b shows the calibration curve obtained for Ferric by IR-783 at 555 nm for pH-3.6. The response shown in FIG. 4a is used in conjunction with the calibration curve shown in FIG. 4b to ascertain the concentration of Ferric iron in the aqueous solution samples. Below is a table containing the raw data shown in FIG. 4a.

| Concentration of $Fe^{3+}$ in Aqueous Solution (ppm) | Absorption at 775 nm | Absorption at 650 nm | Absorption at 555 nm | Absorption at 555 nm-775 nm |
|---|---|---|---|---|
| 0.87 | 1.2249 | 0.17763 | 0.73094 | −0.49396 |
| 0.435 | 1.9115 | 0.26243 | 0.36368 | −1.54782 |
| 0.217 | 2.4412 | 0.33198 | 0.13295 | −2.30825 |
| 0 - Deionized Water | 2.659 | 0.35413 | 0.0366 | −2.62242 |

Figure 4C:
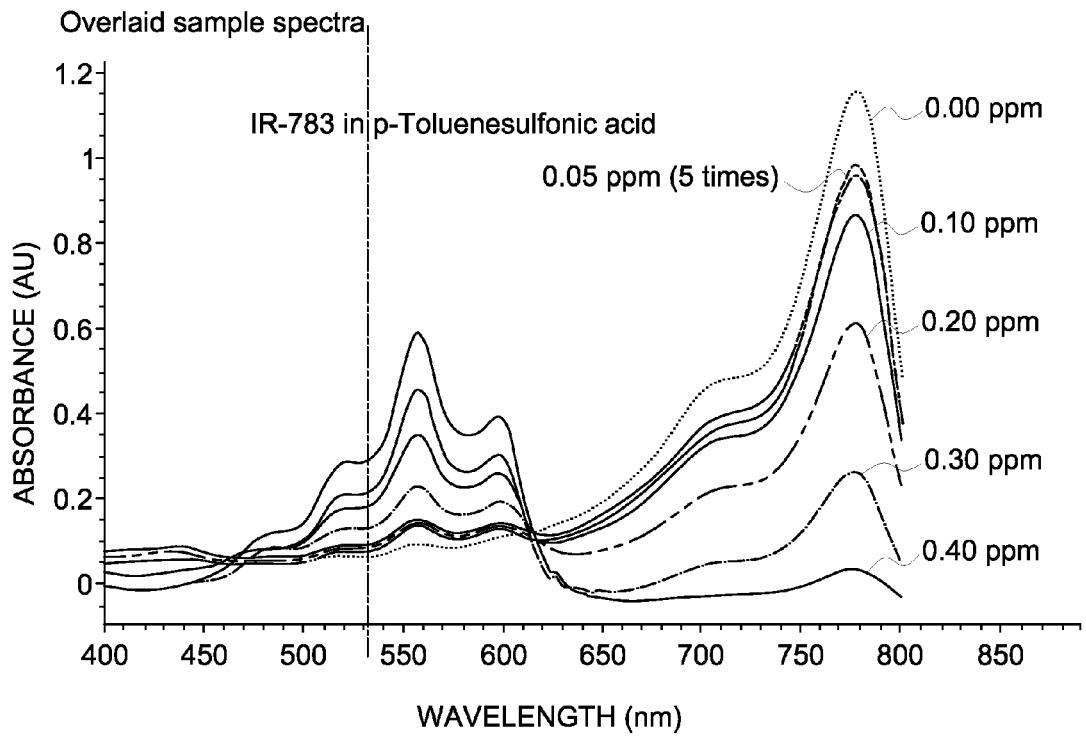
FIG. 4c depicts spectrums of aqueous solutions with different amounts of Ferric iron.
Figure 4D:
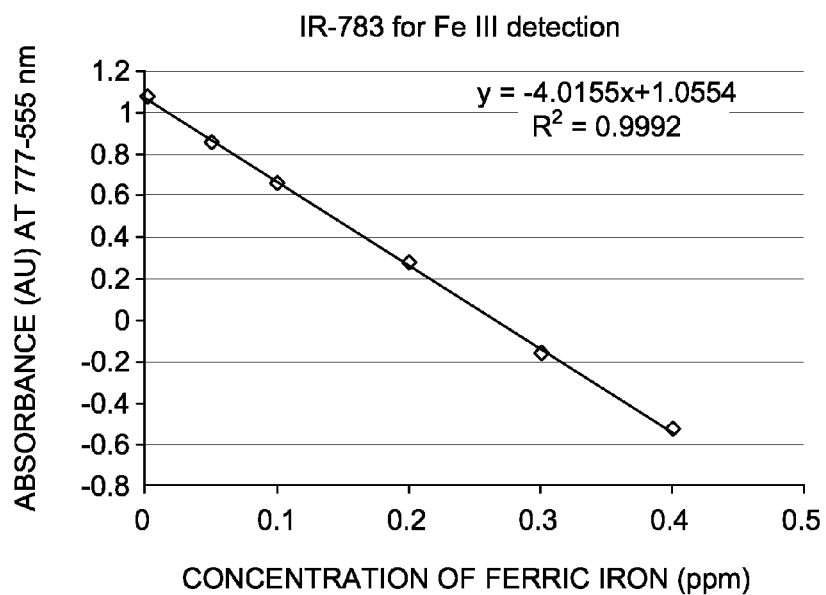
FIG. 4d depicts a calibration curve obtained for Ferric iron using IR-783.

Other buffers can also be used for Ferric ($Fe^{3+}$) detection. For example, 0.5 ml of para-toluenesulfonic acid (0.1M) and 2.0 ml of Ferric standard solution with 25 ul of IR-783 dyes (1 mg/g in ethylene glycol and methanol solvent) will provide a fast reaction at pH=1.2. Raw data and spectrum change are shown in the following Figures. The 0.05 ppm was repeated five times to calculate the standard deviation (SD) of 0.00495. Then by the definition of detection limit (DL), the detection limit is 3.7 ppb (3*SD/slope) given the lab conditions. In one embodiment of the invention, the detection limit is further improved through the use of an automatic sampling and detection system. FIG. 4d shows the calibration curve obtained for Ferric by IR-783 at 555 nm and 777 nm in the presence of a para-toluenesulfonic acid buffer for pH-1.2. The response shown in FIG. 4c is used in conjunction with the calibration curve shown in FIG. 4d to ascertain the concentration of Ferric iron in the aqueous solution samples. As can be seen, this method can detect the presence of Ferric at a concentration as low as about 0.05 ppm. Below is a table containing the raw data shown in FIG. 4c.

| Concentration of Ferric in Aqueous Solution (ppm) | Absorption at 777 nm | Absorption at 555 nm | Absorption at 777 nm-555 nm |
|---|---|---|---|
| 0 - Deionized Water | 1.1684 | .0924 | 1.08 |
| 0.05 | .99882 | .14587 | .853 |
| .1 | .87892 | .23052 | .648 |
| .2 | .62502 | .34983 | .275 |
| .3 | .27622 | .45262 | −.176 |
| .4 | .0463 | .58365 | −.537 |
| .05 | .99485 | .13912 | .856 |
| .05 | .99569 | .15246 | .843 |
| .05 | .97208 | .12531 | .847 |
| .05 | .99456 | .14398 | .851 |

Figure 4E:
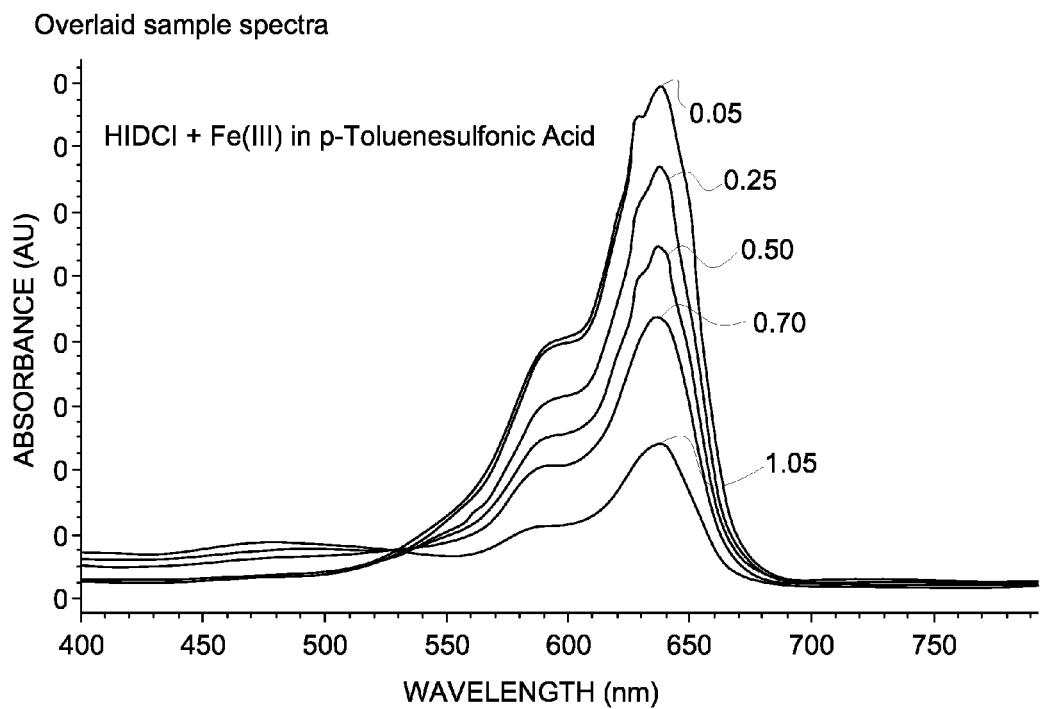
FIG. 4e depicts spectrums of aqueous solutions with different amounts of Ferric iron in the presence of HIDCI.
Figure 4F:
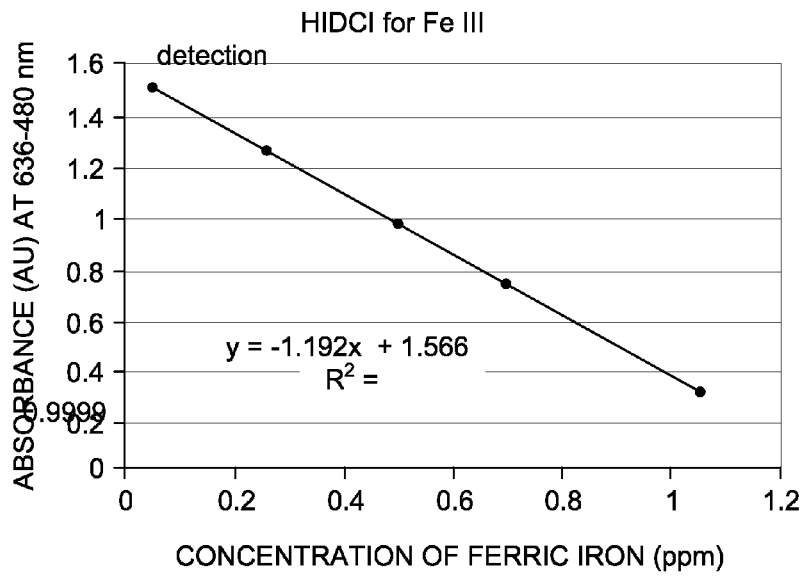
FIG. 4f depicts a calibration curve obtained for Ferric iron using HIDCI.

To further demonstrate the general nature of cyanine dyes response to Ferric (Fe (III)), another dye was tested, HIDCI (1,1,3,3,3',3'-Hexamethylindodicarbocyanine iodide). In this test, 0.5 ml of para-toluenesulfonic and (0.1M) was used as buffer to provide pH as 1.2. Then mixed with 2 ml of different concentration of Ferric standard solutions, 25 ul of HIDCI dye in ethylene glycol and methanol. FIG. 4f shows the calibration curve obtained for Ferric by HIDCI at 480 nm and 636 nm in the presence of para-toluenesulfonic acid for pH-1.2. The response shown in FIG. 4e is used in conjunction with the calibration curve shown in FIG. 4f to ascertain the concentration of Ferric iron in the aqueous solution samples. As can be seen, increasing the concentration of Ferric bleaches the dye HIDCI such that only a weak peak results around 480 nm. As can be seen, this method can detect the presence of Ferric at a concentration as low as about 0.05 ppm.

| Concentration of Ferric in Aqueous Solution (ppm) | Absorption at 480 nm | Absorption at 636 nm | Absorption at 636 nm-480 nm |
|---|---|---|---|
| 1.05 | .16872 | .48106 | .31234 |
| .5 | .12224 | 1.0854 | .96316 |
| .26 | .073261 | 1.3303 | 1.257039 |
| .7 | .1472 | .88657 | .73937 |
| .05 | .065492 | 1.5688 | 1.503308 |
| .05 | .056511 | 1.5621 | 1.505589 |
| .05 | .058116 | 1.5689 | 1.510784 |

Further, IR-783 can also be used to detect the total iron in an aqueous solution sample. The total iron is the sum of both ferrous and Ferric iron. The total iron is detected by oxidizing the ferrous iron to Ferric iron and measuring the Ferric iron. As can be seen, this example shows that cyanine dyes can be used to detect both Ferric and total iron in an aqueous solution down to the parts-per-billion level. It is also anticipated that other cyanine dyes, such as HIDCI, IR-780, IR-755, and IR-746, which exhibit behavior similar to that of IR-783, can also be used.

In another embodiment, it is contemplated that in addition to using IR-783, which responds to Ferric at both 780 nm and 550 nm, another indicator can also be used that responds specifically to ferrous at around 550 nm, such as Ferrozine, TPTZ (2,4,6-Tris(2-pyridyl)-s-triazine). This would allow for simultaneous acquisition of both the ferrous and Ferric iron concentrations in an aqueous solution sample.

EXAMPLE 5

Cyanine Dyes for Polyelectrolytic Detection

This method can also be used for detecting polyelectrolytes including, but not limited to, polyanionic and polycationic polyelectrolytes. Polyelectrolytes are widely used in water treatment for cooling water, boiler water, and wastewater treatment. Polyelectrolytic detection is of interest because when used as a scale inhibitor, the concentration of polyelectrolytic must be maintained above a certain level. Polymers that can be used as scale inhibitors include, but are not limited to, HPS-1 and Coag139D.

Further, polyelectrolytic detection is of interest because the discharge of toxic polyelectrolytes into water systems must be monitored, especially when the water system is natural. Additionally, polyelectrolytic detection is of interest because high polyelectrolytic concentrations might block the function of a membrane during wastewater treatment. Further, the need for low polymer concentration (ppb level) detection is extremely desirable for certain applications, such as boiler feedwater.

These experiments were performed using IR-783, IR-780, and IR-775, which produced a similar result. It is also anticipated that other cyanine dyes, such as IR-746, which exhibits behavior similar to that of IR-780, IR-755, and IR-783, can also be used.

IR-775 for Coag139D at pH=7

Figure 5A:
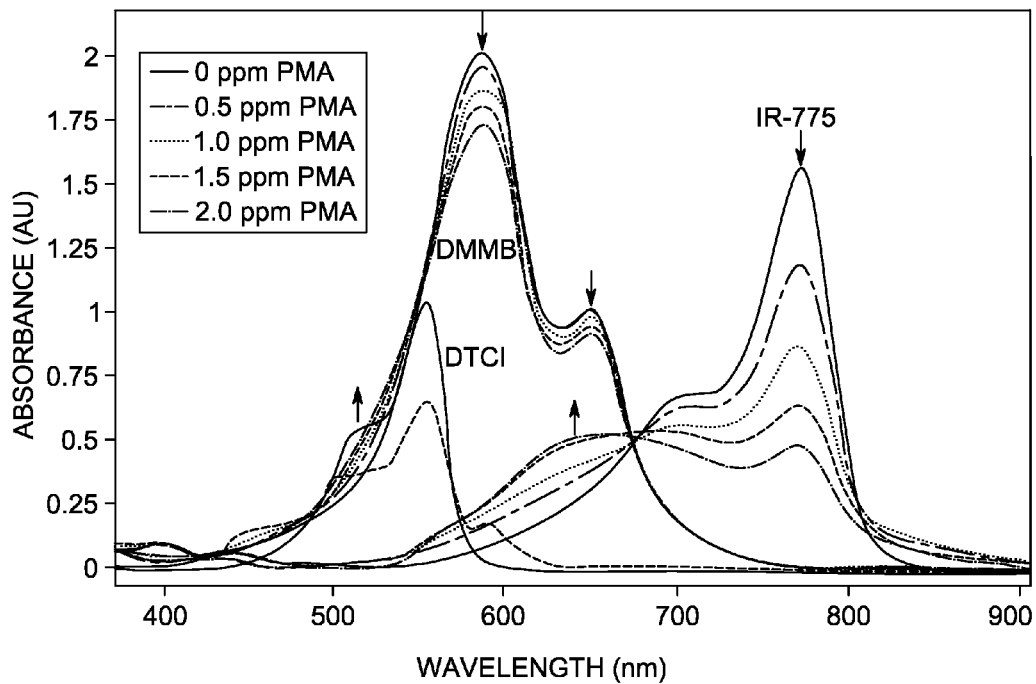
FIG. 5a depicts spectrums of aqueous solutions with different amounts of Coag139D.
Figure 5B:
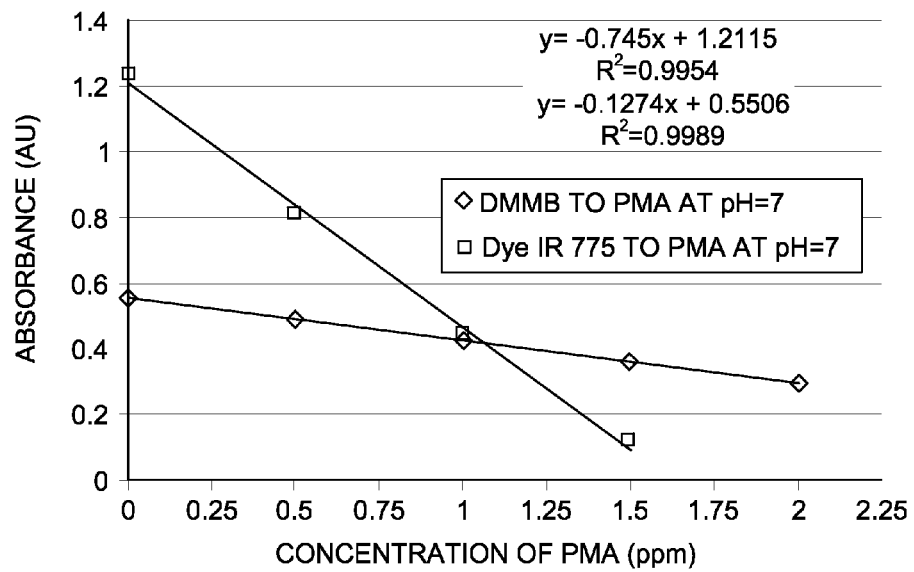
FIG. 5b depicts a calibration curve obtained for Coag139D using IR-775 and DMMB.

FIG. 5a shows spectra of an aqueous solution with differing amounts of Coag139D. More specifically, the response of IR-775 to an aqueous sample solution of Coag139D. Coag139D is also known as PMA. In this example, one part 0.5 ppm IR-775 and one part buffer (pH=7) were added to 3 parts Coag139D sample solution. FIG. 5b shows the calibration curves obtained for Coag139D by IR-775 for 768 nm-648 nm and by DMMB for 525 nnm-648 nm respectively. The response shown in FIG. 5a is used in conjunction with the calibration curve shown in FIG. 5b to ascertain the concentration of Coag139D in the aqueous solution. The response of DMMB (Dimethyl Methylene Blue) to Coag139D is also shown on FIGS. 5a and 5b for comparison purposes. As one can see, the sensitivity of IR-775 is much higher than DMBB. This great sensitivity of IR-775 allows for the detection of Coag139D and other polyanionics at ppb levels.

IR-780 for Coag139D at pH=7

Figure 6A:
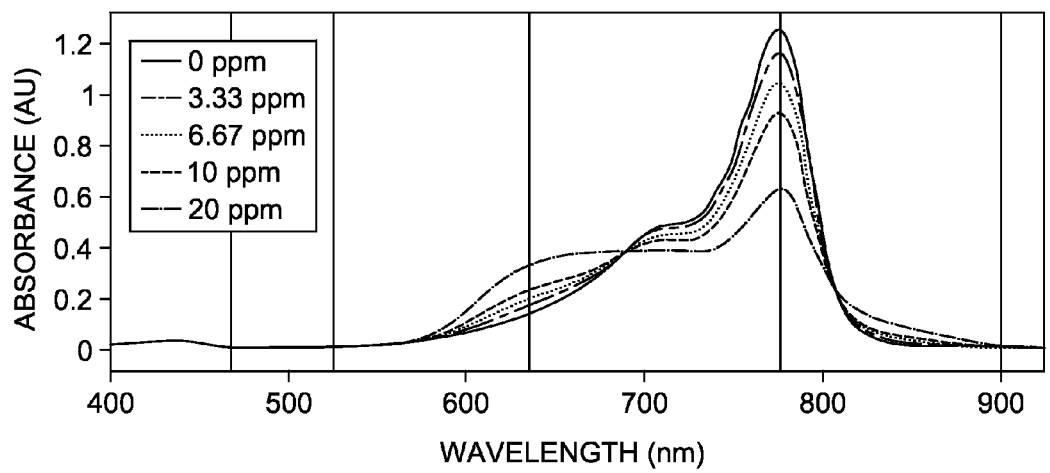
FIG. 6a depicts spectrums of aqueous solutions with different amounts of Coag139D.
Figure 6B:
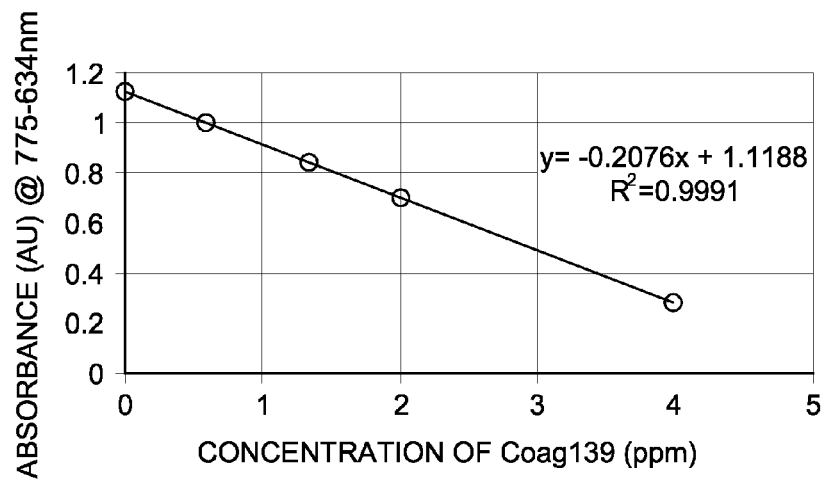
FIG. 6b depicts a calibration curve obtained for Coag139D using IR-780.

FIG. 6a shows the spectra of an aqueous solution with differing amounts of Coag139D. More specifically, the response of IR-780 to Coag139D. In this example, one part 0.5 ppm and one part buffer (pH=7) were added to 3 parts Coag139D aqueous solution. FIG. 6b shows the calibration curve obtained for Coag139D for 775 nm-634 nm. The response shown in FIG. 6a is used in conjunction with the calibration curve shown in FIG. 6b to ascertain the concentration of Coag139D in the aqueous solution. Below is a table containing the raw data shown in FIG. 6a.

| Aqueous Solution (ppm) | Absorption at 467 nm | Absorption at 525 nm | Absorption at 634 nm | Absorption at 775 nm | Absorption at 900 nm | Coag 130D active polymer concentration (ppm) | 775 nm-634 nm |
|---|---|---|---|---|---|---|---|
| 0 ppm deionized | 0.011 | 0.0108 | 0.14493 | 1.2551 | 0.00537 | 0 | 1.11017 |
| 20 m ppm | 0.0108 | 0.00663 | 0.33137 | 0.62108 | 0.0104 | 4 | 0.28971 |
| 10 ppm | 0.00870 | 0.00703 | 0.23372 | 0.92677 | 0.00611 | 2 | 0.69305 |
| 3.33 ppm | 0.0104 | 0.00941 | 0.17522 | 1.1675 | 0.00389 | 0.667 | 0.99228 |
| 6.67 ppm | 0.00711 | 0.00604 | 0.2001 | 1.0467 | 0.00394 | 1.34 | 0.8466 |

IR-780+HPS-I for polyDADMAC

PolyDADMAC (Polydiallyldimethylammonium chloride), has a number of applications. PolyDADMAC is used in waste water treatment as a primary organic coagulant which neutralizes negatively charged colloidal material and reduces sludge volume compared with inorganic coagulants. In the pulp and paper industry, PolyDADMAC is used for controlling disturbing substances in the papermaking process. In addition, it can be used to improve the efficiency of disk filters and flotators, and for cationization of fillers to provide maximal filler retention. PolyDADMAC can also be used as a flocculant to improve soap separation process in the evaporation plant of kraft pulp mills thus contributing to higher tall oil yield. In water purification, PolyDADMAC is used as flocculent. It is very effective in flocculating, decoloring, killing algae and removing organics, such as humus. Only a small amount of PolyDADMAC is necessary to produce large flocs, rapid precipitation and low turbidity residue.

polyDADMAC in the aqueous solution. Below is a table containing the raw data shown in FIG. 7a. As can be seen, this method can detect the presence of polyDADMAC at a concentration as low as about 0.048 ppm.

| Aqueous Solution (ppm) | Absorption at 520 nm | Absorption at 595 nm | Absorption at 630 nm | Absorption at 780 nm | Absorption at 950 nm | PolyDADMAC concentration/ (ppm) | Abs (780 nm-950 nm) |
|---|---|---|---|---|---|---|---|
| 0.3 HPS-I, deionized water | 0.00173 | 0.0601 | 0.11936 | 0.13161 | −0.000570 | 0 | 0.132 |
| 0.24 ppm polyDADMAC | 0.00359 | 0.0507 | 0.0936 | 0.2235 | 0.00182 | 0.24 | 0.222 |
| 0.11 ppm polyDADMAC | 0.00519 | 0.0548 | 0.11143 | 0.16146 | 0.00171 | 0.11 | 0.160 |
| 0.48 ppm polyDADMAC | 0.00139 | 0.0302 | 0.068 | 0.31539 | −0.00105 | 0.48 | 0.316 |
| 0.048 ppm polyDADMAC | 0.0000262 | 0.0563 | 0.11703 | 0.13471 | −0.00244 | 0.048 | 0.137 |
| 0.78 ppm polyDADMAC | 0.000855 | 0.0163 | 0.0449 | 0.42398 | −0.00209 | 0.72 | 0.426 |
| 0.078 ppm polyDADMAC | 0.00156 | 0.0638 | 0.1216 | 0.14329 | −0.00154 | 0.072 | 0.145 |
| 0 ppm polyDADMAC | −0.000614 | 0.0588 | 0.11864 | 0.12858 | −0.00285 | 0 | 0.131 |

However, PolyDADMAC is thought to have adverse effects on aquatic organisms. Thus, the discharge of polyDADMAC is highly regulated. For example, the GE water process and technologies data show in the aquatic toxicology for ceriodaphnia 48 hour static renewal bioassay, LC50=0.34 ppm; No Effect Level=0.25 ppm, thus a method to detect such low or even lower concentrations is needed. Accordingly, a detection limit of 1/10 of the No effect level, or 0.025 ppm, is desirable. A detection limit of 0.025 ppm is normally very hard to obtain using common dyes with relative low molar extinction coefficient.

Figure 7A:
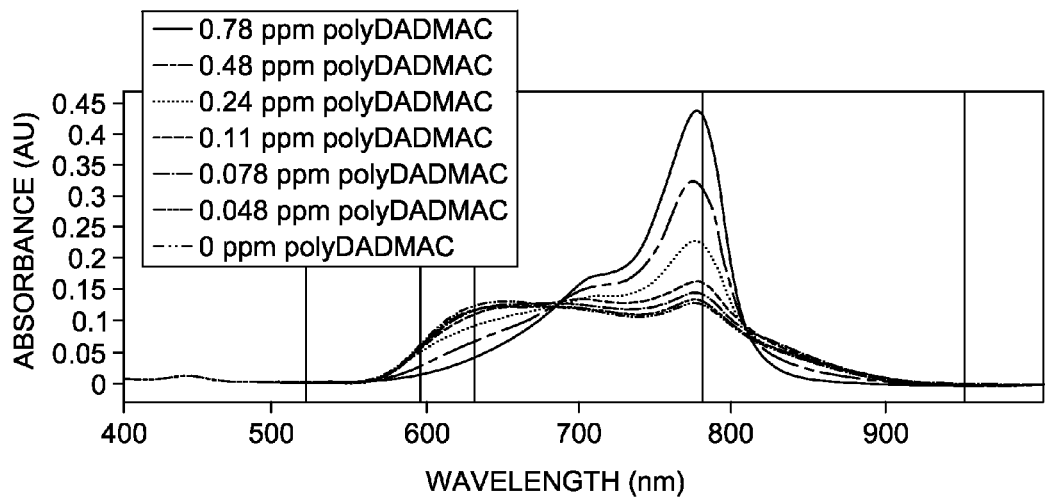
FIG. 7a depicts spectrums of aqueous solutions with different amounts of polyDADMAC.

FIG. 7a shows the spectra of an aqueous solution with differing amounts of polyDADMAC. The mechanism is described herein. IR-780 is a cationic dye, HPS-I is a negatively charged polymer, and interaction between IR-780 with HPS-I significantly depresses the absorbance peak at 780 nm and shifts the maximum peak to 630 nm. However, by adding polyDADMAC into the solution mixture, polyDADMAC competitively interacts with HPS-I and then releases IR-780 to free state and retrieves the absorbance spectrum. More specifically, the response of IR-780 with HPS-I (from GE Betz of Trevose, Pa.) to an aqueous solution of polyDADMAC. As can be seen, the product of IR-780 and HPS-I has a maximum peak around 630 nm. The blue shift of the maximum peak from 780 nm to 630 nm is caused by the aggregation of IR-780 through the HPS-I backbone via electric interaction. Accordingly, since polyDADMAC is positively charged, when polyDADMAC was placed in fluid communication with the mixture of IR-780 and HPS-I, the stronger interaction of polyDADMAC with HPS-I release dye IR-780, thus retrieving the spectrum of IR-780 as shown in FIG. 7a.

Figure 7B:
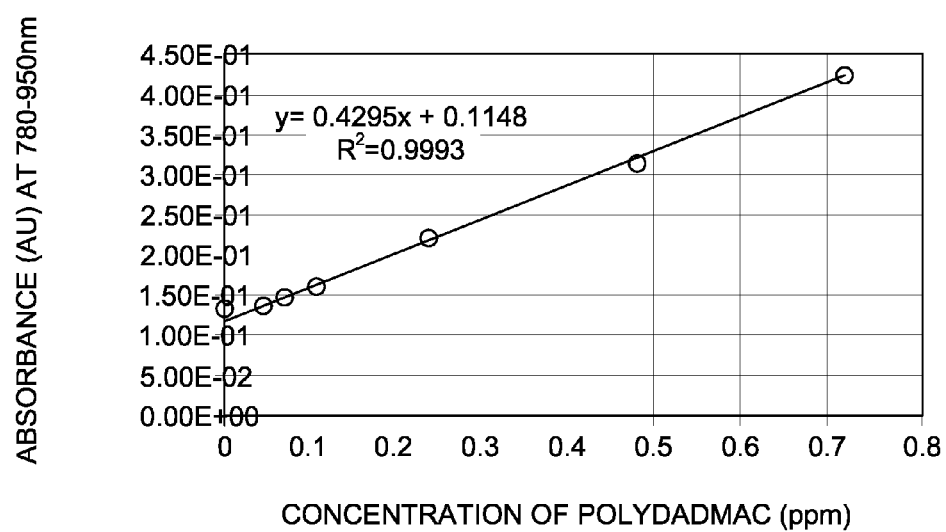
FIG. 7b depicts a calibration curve obtained for polyDADMAC using IR-780.
Figure 8A:
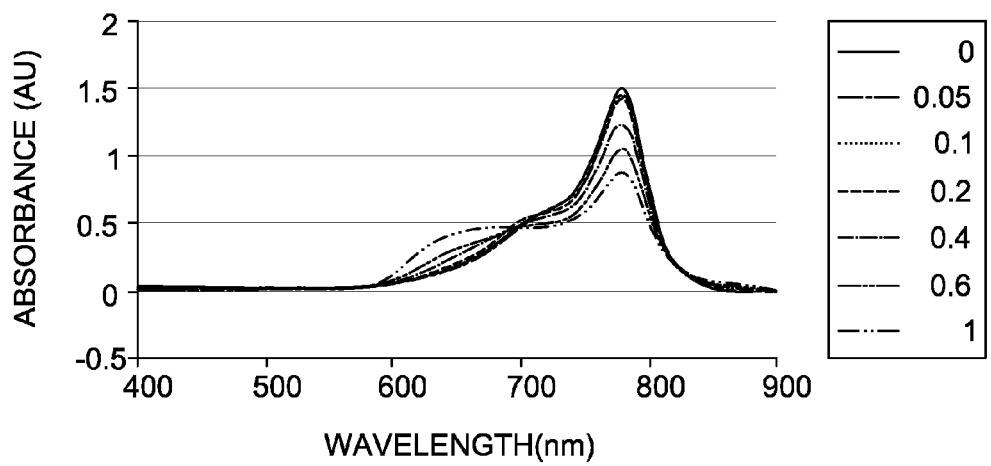
FIG. 8a depicts spectrums of aqueous solutions with different amounts of polyDADMAC.
Figure 8B:
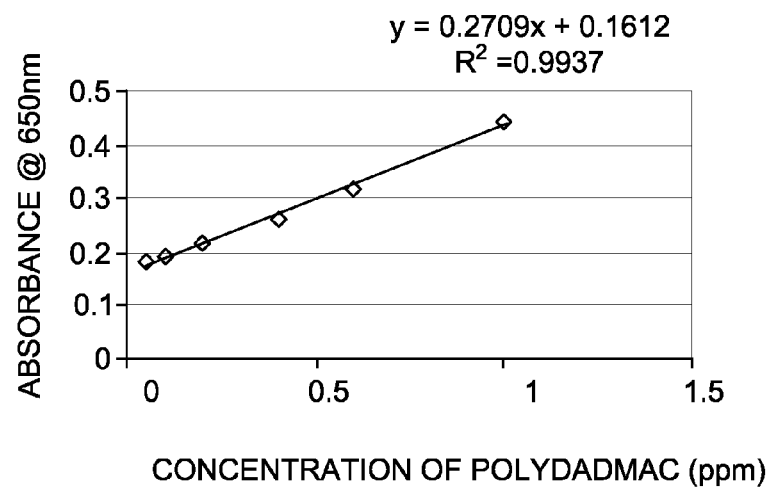
FIG. 8b depicts a calibration curve obtained for polyDADMAC using IR-783.

FIG. 7b shows the calibration curve obtained for polyDADMAC by IR-780 for 780 nm-950 nm. The response shown in FIG. 7a is used in conjunction with the calibration curve shown in FIG. 7b to ascertain the concentration of IR-783 for polyDADMAC IR-783 has two sulfuric groups, which can electrically associate with polyDADMAC, thus resulting in a spectrum change. The change of spectrum is proportional to the concentration of polyDADMAC. Accordingly, the concentration of polyDADMAC for an unknown sample could be calculated from the spectrum change. FIG. 8b shows the calibration curve obtained for polyDADMAC by IR-783 for 650 nm. The response shown in FIG. 8a is used in conjunction with the calibration curve shown in FIG. 8b to ascertain the concentration of polyDADMAC in the aqueous solution. As can be seen, this method can detect the presence of polyDADMAC at a concentration as low as about 0.05 ppm.

While this invention has been described in conjunction with the specific embodiments described above, it is evident that many alternatives, combinations, modifications and variations are apparent to those skilled in the art. Accordingly, the preferred embodiments of this invention, as set forth above are intended to be illustrative only, and not in a limiting sense. Various changes can be made without departing from the spirit and scope of this invention. Therefore, the technical scope of the present invention encompasses not only those embodiments described above, but also all that fall within the scope of the appended claims.

This written description uses examples to disclose the invention, including the best mode, and also to enable any person skilled in the art to practice the invention, including making and using any devices or systems and performing any incorporated processes. The patentable scope of the invention is defined by the claims, and may include other examples that occur to those skilled in the art. These other examples are intended to be within the scope of the claims if they have structural elements that do not differ from the literal language of the claims, or if they include equivalent structural elements with insubstantial differences from the literal language of the claims.

What is claimed is:

1. A method of measuring the concentration of an analyte in an aqueous solution that comprises the steps of:
   obtaining an aqueous solution containing an analyte, wherein said analyte is iron;

providing a cyanine indicator; wherein said cyanine indicator is selected from the group consisting of 1,1',3,3,3',3'-hexamethylindodicarbocyanine iodide, 2-[2-[2-chloro-3-[2-[1,3-dihydro-3,3-dimethyl-1-(4-sulfobutyl)-2H-indol-2-ylidene]-ethylidene]-1-cyclohexen-1-yl]-ethenyl]-3,3-dimethyl-1-(4-sulfobutyl)-3H-indolium hydroxide, 1,1',3,3,3',3'-4,4',5,5'-di-benzo-2,2'-indotricarbocyanine perchlorate, 2-[2-[2-chloro-3-[2-(1,3-dihydro-1,3,3-trimethyl-2H-indol-2-ylidene)-ethylidene]-1-cyclohexen-1-yl]-ethnyl]-1,3,3-trimethyl-3H-indolium chloride, and 2-[7-[1,3-dihydro-3,3-dimethyl-1-(4-sulfobutyl)-2H-indol-2-ylidene]-hepta-1,3,5-trienyl]-3,3-dimethyl-1-(4-sulfobutyl)-3H-indolium hydroxide placing said aqueous solution in fluid communication with said cyanine indicator;

measuring an absorbance change of said cyanine indicator; and comparing the absorbance change of said cyanine indicator with a calibration curve of the absorbance change of samples containing known concentrations of said analyte to determine the concentration of said analyte;

wherein said absorbance change is proportional to the concentration of said analyte in said aqueous solution.

2. The method of claim 1, wherein said cyanine indicator is aqueous.

3. The method of claim 1, wherein said cyanine indicator is contained in a film.

4. The method of claim 3, wherein the dry film thickness of said film is between about 1 μm to about 20 μm.

5. The method of claim 1, wherein said method measures said analyte down to a level of about 0.2 ppm.

6. The method of claim 1, further comprising adding to said aqueous solution at least one oxidizer when said iron is total iron comprising ferrous iron and ferric iron therein, and wherein said cyanine indicator responds to ferric iron at around 550 nm.

7. A method of measuring the concentration of an analyte in an aqueous solution that comprises the steps of:

obtaining an aqueous solution containing an analyte, wherein said analyte is a polyelectrolyte;

adding to said aqueous solution at least one compound, wherein said compound is a buffer;

providing a cyanine indicator; wherein said cyanine indicator is selected from the group consisting of 1,1',3,3,3',3'-hexamethylindodicarbocyanine iodide, 2-[2-[2-chloro-3-[2-[1,3-dihydro-3,3-dimethyl-1-(4-sulfobutyl)-2H-indol-2-ylidene]-ethylidene]-1-cyclohexen-1-yl]-ethenyl]-3,3-dimethyl-1-(4-sulfobutyl)-3H-indolium hydroxide, 1,1',3,3,3',3'-4,4',5,5'-di-benzo-2,2'-indotricarbocyanine perchlorate, 2-[2-[2-chloro-3-[2-(1,3-dihydro-1,3,3-trimethyl-2H-indol-2-ylidene)-ethylidene]-1-cyclohexen-1-yl]-ethnyl]-1,3,3-trimethyl-3H-indolium chloride, and 2-[7-[1,3-dihydro-3,3-dimethyl-1-(4-sulfobutyl)-2H-indol-2-ylidene]-hepta-1,3,5-trienyl]-3,3-dimethyl-1-(4-sulfobutyl)-3H-indolium hydroxide;

placing said aqueous solution in fluid communication with said cyanine indicator;

measuring an absorbance change of said cyanine indicator; and comparing the absorbance change of said cyanine indicator with a calibration curve of the absorbance change of samples containing known concentrations of said analyte to determine the concentration of said analyte;

wherein said absorbance change is proportional to the concentration of said analyte in said aqueous solution.

8. The method of claim 7, wherein said polyelectrolyte comprises at least one member selected from the group consisting of hydroxypropyl sulfonate ether copolymers, alcohol ether carboxylates, alkylphenol ethoxylates, polymethacrylic acid, and polydiallyldimethyldiammonium chloride.

9. The method of claim 7, wherein said buffer has a pH of about 7.

10. The method of claim 7, wherein said cyanine indicator is aqueous.

11. The method of claim 7, wherein said cyanine indicator is contained in a film.

12. The method of claim 11, wherein the dry film thickness of said film is between about 1 μm to about 20 μm.

13. The method of claim 12, wherein said method measures said analyte down to a level of about 0.2 ppm.

\* \* \* \* \*